(12) United States Patent
Kaal et al.

(10) Patent No.: US 8,021,333 B2
(45) Date of Patent: Sep. 20, 2011

(54) SYRINGE SPRING RETAINER

(75) Inventors: Joseph Hermes Kaal, Morpeth (AU); Craig Stephen Thorley, Largs (AU)

(73) Assignee: Unitract Syringe Pty Ltd., Sydney, New South Wales (AU)

( * ) Notice: Subject to any disclaimer, the term of this patent is extended or adjusted under 35 U.S.C. 154(b) by 1436 days.

(21) Appl. No.: 10/549,710

(22) PCT Filed: Mar. 19, 2004

(86) PCT No.: PCT/AU2004/000354
§ 371 (c)(1), (2), (4) Date: Jun. 15, 2006

(87) PCT Pub. No.: WO2004/082747
PCT Pub. Date: Sep. 30, 2004

(65) Prior Publication Data
US 2006/0235354 A1    Oct. 19, 2006

(30) Foreign Application Priority Data

Mar. 20, 2003 (AU) ............................ 2003901301
Sep. 18, 2003 (AU) ............................ 2003905080

(51) Int. Cl.
*A61M 5/00* (2006.01)
*A61M 5/315* (2006.01)

(52) U.S. Cl. ...................................... 604/110; 604/220
(58) Field of Classification Search ................. 604/110, 604/192, 198, 218, 220, 226, 240
See application file for complete search history.

(56) References Cited

U.S. PATENT DOCUMENTS

| 5,112,316 | A | | 5/1992 | Venturini | |
|---|---|---|---|---|---|
| 5,167,641 | A | | 12/1992 | Schmitz | |
| 5,180,370 | A | | 1/1993 | Gillespie | |
| 5,201,720 | A | * | 4/1993 | Borgia et al. | 604/198 |
| 5,324,265 | A | | 6/1994 | Murray et al. | |
| 5,411,487 | A | * | 5/1995 | Castagna | 604/198 |

(Continued)

FOREIGN PATENT DOCUMENTS

EP    0347742 B1    9/1992

(Continued)

OTHER PUBLICATIONS

Japanese Office Action for Japanese Application No. 2006-503971 (Apr. 5, 2010).

*Primary Examiner* — Theodore Stigell
*Assistant Examiner* — Andrew Gilbert
(74) *Attorney, Agent, or Firm* — LeClairRyan

(57) ABSTRACT

A spring retainer (60) for a syringe (10) that has a barrel (40), a plunger (20), a spring (90) and a retractable needle (50) that can couple with the plunger for spring-driven retraction of the coupled needle and plunger. The spring retainer has first (70) and second (80) body members that cooperate to releasably maintain the spring in a compressed state until the plunger is coupled to the retractable needle after depression of the plunger to deliver the fluid contents of the syringe. Depression of the plunger triggers rotational disengagement of the first and second body members to allow decompression of the spring which forces retraction of the needle into the barrel. Rotational disengagement of the first and second body members also assists rotation of the plunger into a final, inoperable position.

16 Claims, 8 Drawing Sheets

U.S. PATENT DOCUMENTS

| | | | |
|---|---|---|---|
| 5,429,613 A * | 7/1995 | D'Amico | 604/198 |
| 5,762,634 A * | 6/1998 | Davis | 604/195 |
| 5,984,898 A | 11/1999 | Garvin | |
| 6,039,713 A | 3/2000 | Botich | |
| 6,083,199 A * | 7/2000 | Thorley et al. | 604/110 |
| 6,090,077 A | 7/2000 | Shaw | |
| 6,221,052 B1 | 4/2001 | Caizza et al. | |
| 6,527,742 B1 * | 3/2003 | Malenchek | 604/110 |
| 6,569,115 B1 | 5/2003 | Barker et al. | |
| 7,033,343 B2 * | 4/2006 | McWethy et al. | 604/506 |
| 7,500,967 B2 * | 3/2009 | Thorley et al. | 604/218 |

FOREIGN PATENT DOCUMENTS

| | | |
|---|---|---|
| EP | 0 566 882 A1 * | 3/1993 |
| EP | 0566882 A1 | 10/1993 |
| EP | 1184049 A1 | 3/2002 |
| FR | 2794650 A1 | 12/2000 |
| WO | 93/12830 A1 | 7/1993 |
| WO | WO 93/25257 A1 | 12/1993 |
| WO | WO 01/30427 A1 | 5/2001 |

* cited by examiner

SYRINGE SPRING RETAINER

This application is a national stage application under 35 U.S.C. §371 from PCT Application No. PCT/AU2004/000354, filed Mar. 19, 2004, which claims the priority benefit of Australian Application Nos. 2003901301, filed Mar. 20, 2003 and 2003905080, filed Sep. 18, 2003.

FIELD OF THE INVENTION

THIS INVENTION relates to a spring retainer for a syringe. More particularly, this invention relates to a spring retainer for a single-use, retractable syringe that facilitates prevention of syringe and/or needle re-use

BACKGROUND OF THE INVENTION

The problems of shared syringes are notorious. The practice of sharing syringes without adequate sterilisation between successive users is a major contributor to the transfer of Human Immunodeficiency Virus and Hepatitis with subsequent severe repercussions for the sufferer of such diseases and at a high cost to society of supporting and providing medical attention to those sufferers.

A lesser but still significant risk associated with unclean needles and syringes arises from the possibility of inadvertent needle-stick injuries. This is particularly a problem for law enforcement officers and paramedics who often encounter users of illegal drugs in their professional activities. Additionally, the habits of illegal drug users are such that dangerous by-products of their activities, such as discarded syringes, are often left in places of public access presenting a risk to the users of areas such as public parks and school grounds.

International Publication WO 01/80930 describes a single-use retractable syringe that is highly effective in preventing syringe re-use by ensuring full depression of the plunger during fluid delivery and by ensuring permanent withdrawal of the needle by the plunger back into the syringe barrel. In particular, retractable syringes such as described in International Publication WO 01/80930, Australian Patent 731159 and U.S. Pat. No. 6,083,199 employ a spring to facilitate needle retraction and thereby prevent syringe re-use.

However, resistance by the spring during plunger depression provides an undesirable "feel" to some syringe users, such as intravenous drug users.

SUMMARY OF THE INVENTION

Therefore, in a broad form the present invention provides a spring retainer for a syringe that provides efficient retraction of a spent needle into the barrel of a retractable syringe while also having improved tactile properties to a syringe user.

In one aspect, the invention provides a spring retainer for a syringe that comprises a barrel, a plunger, a spring and a retractable needle, said spring retainer adapted to releasably maintain said spring in a compressed state until decompression of said spring is required to facilitate retraction of said retractable needle into said barrel.

In another aspect, the invention provides a syringe comprising a barrel, a plunger, a spring retainer and a spring, to which syringe a retractable needle is mountable so as to be capable of coupling with said plunger for retraction of said needle into said barrel, said spring retainer adapted to releasably maintain said spring in a compressed state until decompression of said spring is required to facilitate retraction of said retractable needle into said barrel.

Suitably, the syringe is adapted so that a retractable needle is mountable thereto.

In a preferred embodiment, said syringe is a retractable syringe having a retractable needle, in use said spring is compressed in said retainer until at or near completion of depression of said plunger to inject material from said syringe, de-compression of said spring acting thereafter to facilitate withdrawal of said retractable needle into said barrel.

In a preferred embodiment, said spring retainer has a housing that comprises a first body member and second body member which are releasably engageable to maintain said spring in an initial compressed state.

According to this embodiment, disengagement of said first body member and second body member allows or facilitates decompression of said spring.

Preferably, said plunger comprises means for engaging said housing to trigger, initiate, actuate or otherwise begin disengagement of said first body member and second body member.

Such means may be in the form of one or more shoulders, tabs, flanges or other projections which can engage one or more, respective complementary mating portions of said housing.

Suitably, said one or more, respective complementary mating portions of said housing may be in the form of ramps, slots, depressions, recesses or the like which in use can be engaged by said plunger means for engaging said housing.

Preferably, disengagement of said first body member and second body member is accompanied by rotation of said second body member relative to said first body member, which in turn assists rotation of said plunger, when said retractable needle is coupled therewith, into a final, inoperable position.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

The present invention will now be described with reference to preferred embodiments and with reference to the accompanying drawings, wherein.

DETAILED DESCRIPTION OF THE PREFERRED EMBODIMENTS

It will be appreciated that herein is described an embodiment of a single use retractable syringe 10 comprising in part, components based on those originally described in International Publication WO 01/80930, Australian Patent 731159 and U.S. Pat. No. 6,083,199, each of which is incorporated herein by reference.

Figure 1:
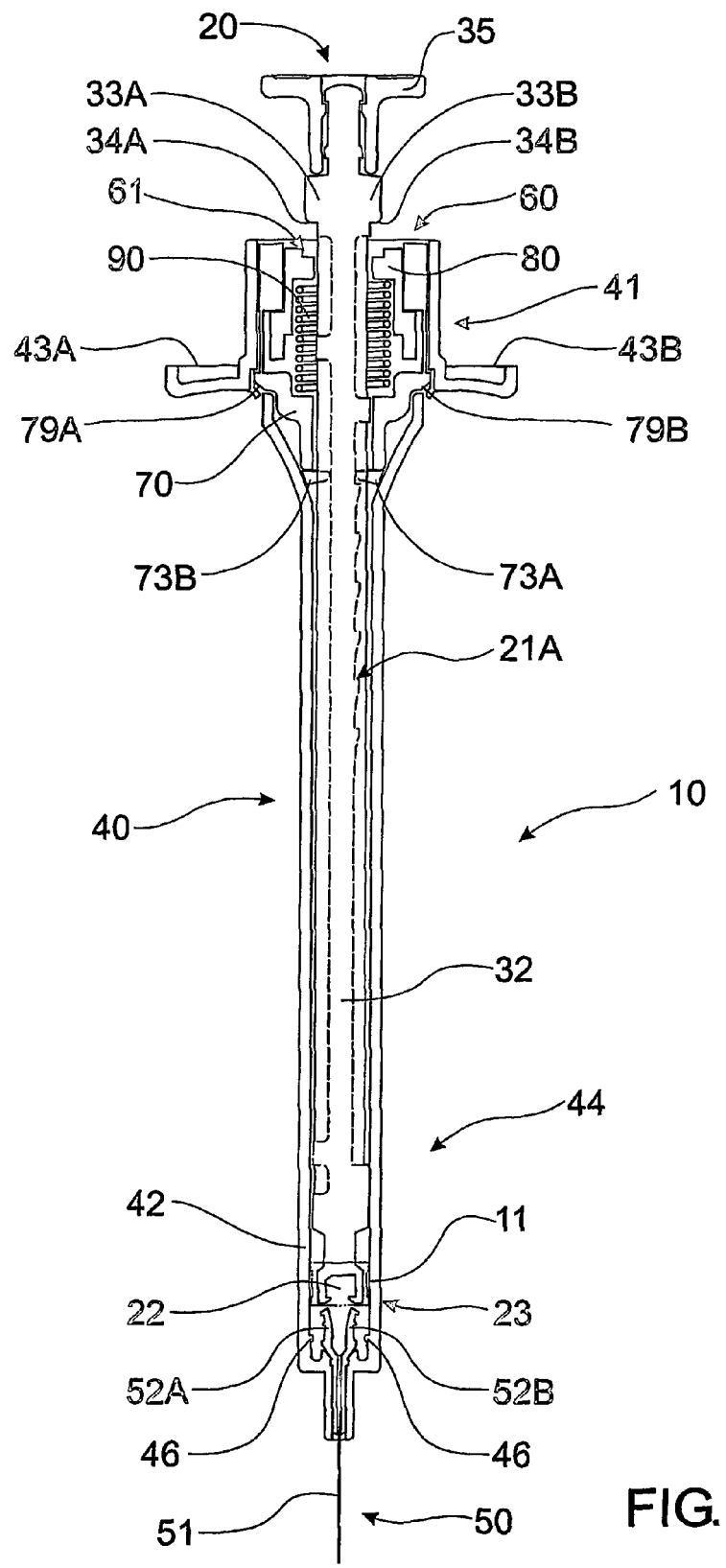
FIG. 1 is a cross-sectional view of a retractable single use syringe.
Figure 2:
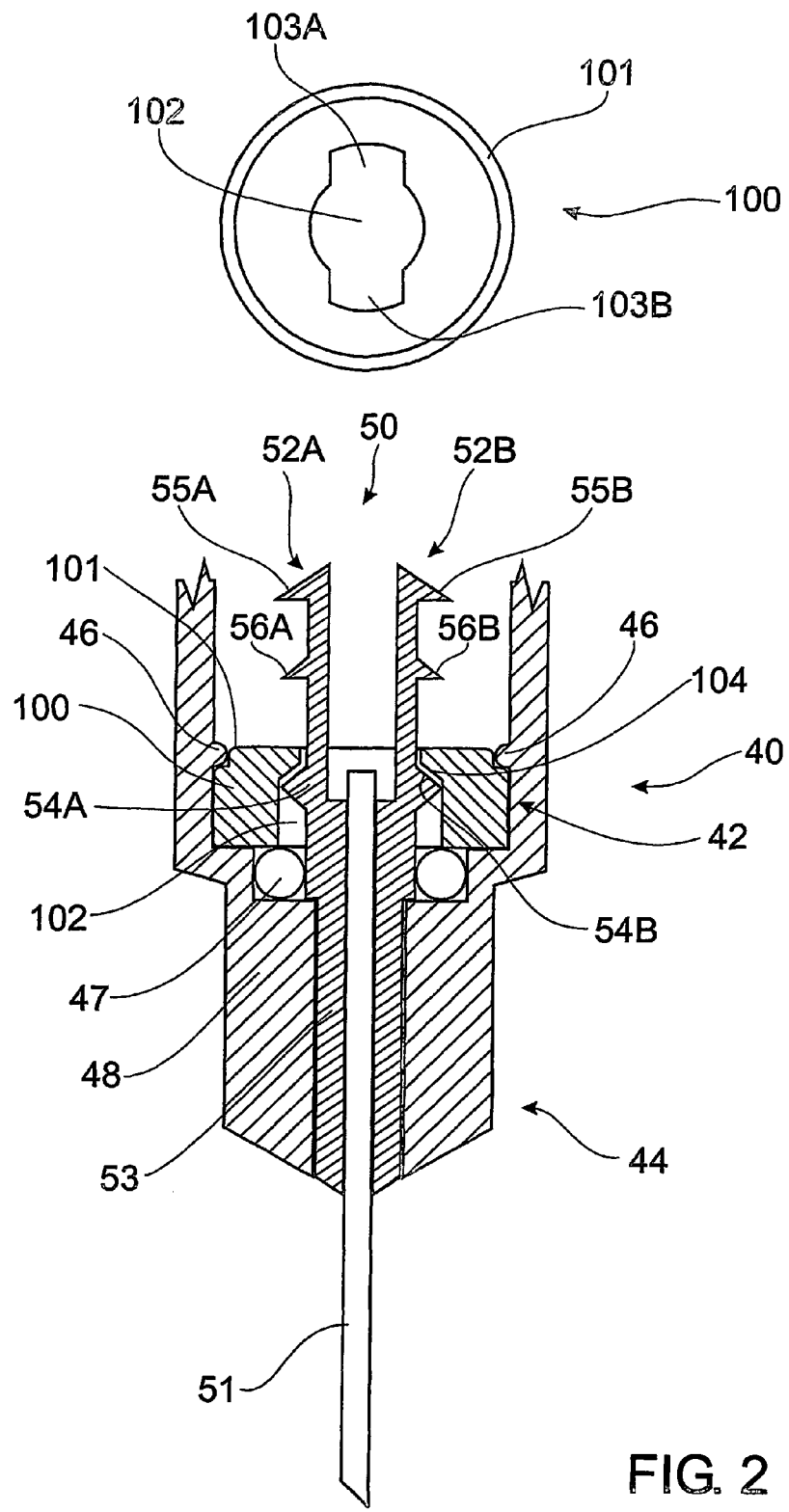
FIG. 2 is a side view of an embodiment of a retractable needle mounted to a syringe barrel.

Referring to FIG. 1 and FIG. 2, syringe 10 has plunger 20, barrel 40, retractable needle 50 and spring retainer 60. Spring retainer 60 is located in flared end 41 of barrel 40, and comprises first body member 70 and second body member 80 that co-operate to house and maintain spring 90 in the initial compressed state shown in FIG. 1. Syringe 10 also comprises seal 11 located on plunger 20, which prevents leakage fluid between plunger 20 and internal wall 42 of barrel 40.

Retractable needle 50 is mounted at needle end 44 of barrel 40 and comprises cannula 51 and barbed arms 52A, 52B mounted to body 53 that are engageable by respective barb-engaging apertures 22 of needle-engaging means 23 in plunger 20 to facilitate retraction of needle 50 at the end of delivery of the fluid contents of syringe 10. This retraction is driven by de-compression of spring 90, as will be described in more detail hereinafter.

Referring particularly to FIG. 2, a preferred embodiment is described wherein retractable needle 50 may be fitted at needle end 44 of barrel 40 by disc member 100 that has indent 101 which co-operates with annular rib 46 on inside wall 42 of barrel 40. O-ring seal 47 is seated in annular step 48 in barrel wall 42. Body 53 of retractable needle 50 has elbows 54A, 54B that are held by annular shoulder 104 of disc member 100 until retraction of retractable needle 50.

It is also noted that according to this embodiment barbed arms 52A, 52B each comprise first barb 55A, 55B and second barb 56A, 56B. First barbs 55A, 55B provide a safety mechanism should second barbs 56A, 56B not properly engage respective barb-engaging apertures 22 to facilitate retraction of retractable needle 50.

That is, first barbs 55A, 55B can engage barb-engaging apertures 22 should second barbs 56A, 56B fail to properly engage respective apertures 22.

Disc member 100 has aperture 102 with recesses 103A, 103B which allow longitudinal movement of elbows 54A, 54B therethrough to allow retraction of needle 50. Alignment of elbows 54A, 54B is achieved when retractable needle 50 is rotated by plunger 20 engaged therewith during retraction, as will be described in more detail hereinafter.

In an alternative embodiment, retractable needle 50 may be provided such as described in Australian Patent 731159 and U.S. Pat. No. 6,083,199.

Figure 3A:
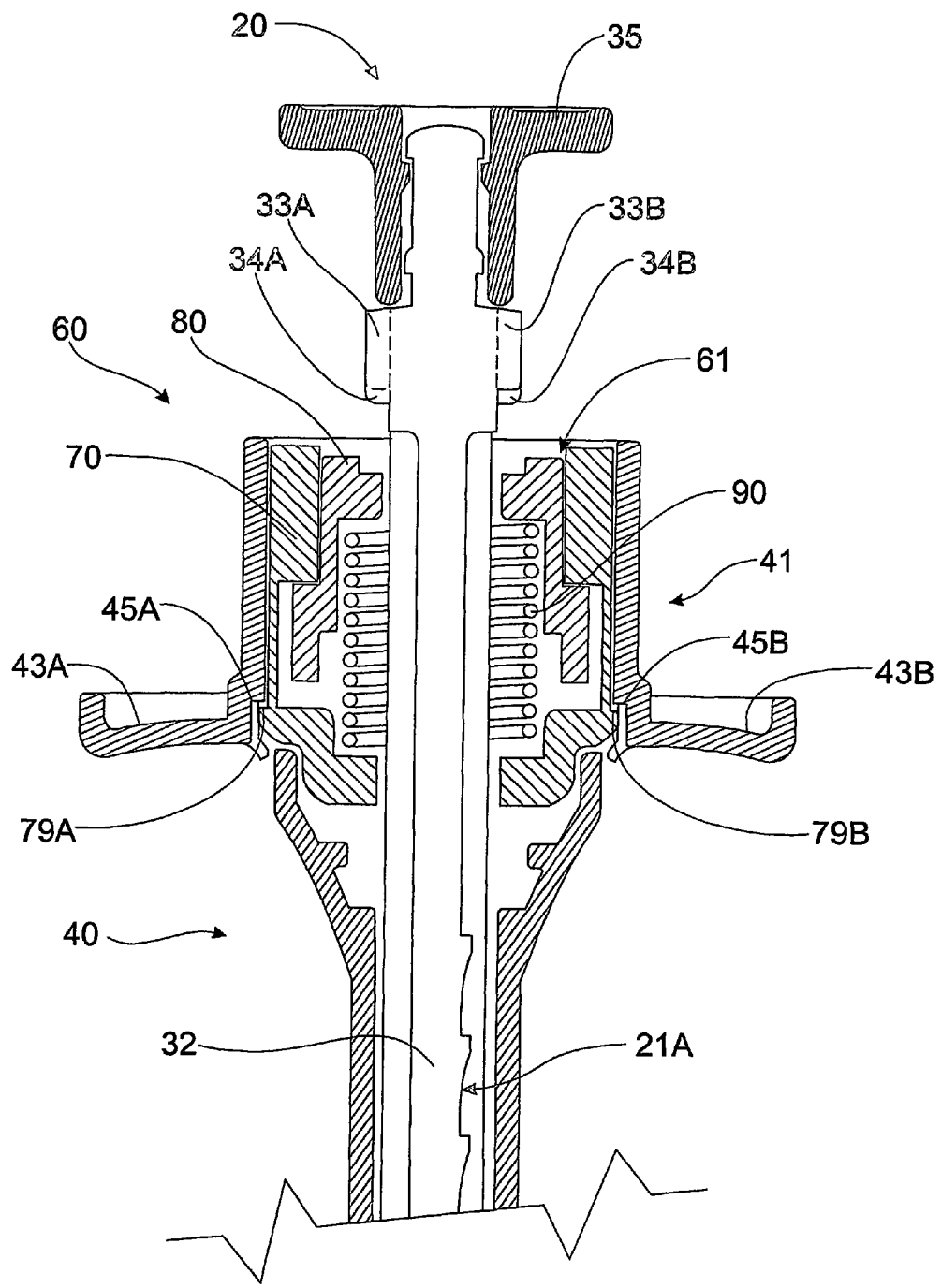
FIGS. 3A and 3B are respective sectional views of a spring retainer mounted to a syringe.
Figure 3B:
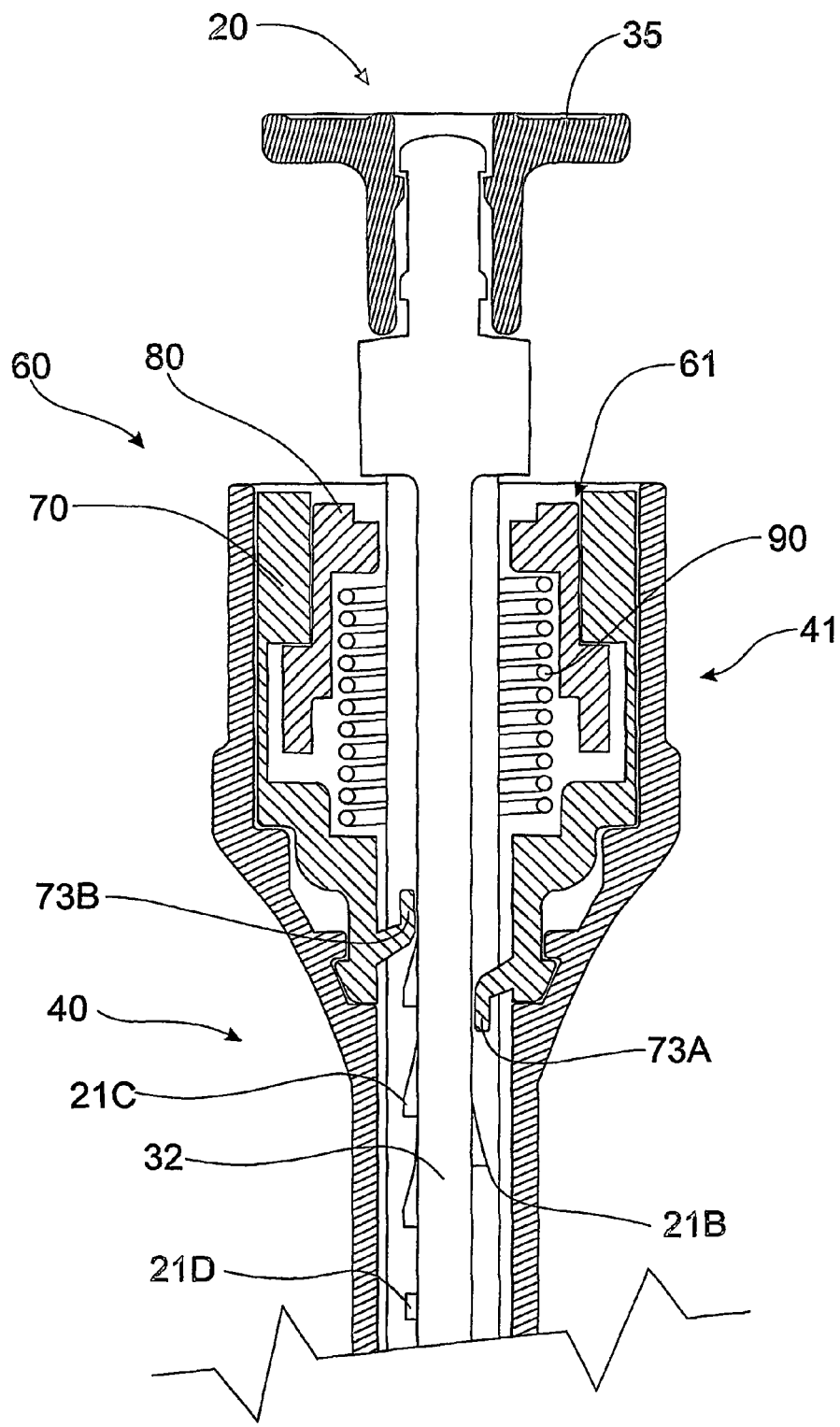

As best seen in FIGS. 3A and 3B, plunger 20 further comprises plunger shaft 32 having shoulders 33A, 33B which respectively have inclined surfaces 34A, 34B and button 35 operable by a user.

Barrel 40 is integrally formed with finger grips 43A, 43B and flared end 41 into which is fitted spring retainer 60.

Spring retainer 60 may be fitted into flared end 41 of barrel 40 such as by an interference fit whereby first body member 70 engages wall 42 of barrel 40 as shown in FIG. 3A. According to this embodiment, first body member 70 is held in barrel 40 by clips 79A, 79B engaging respective steps 45A, 45B in wall 42.

Figures 4A, 4B:
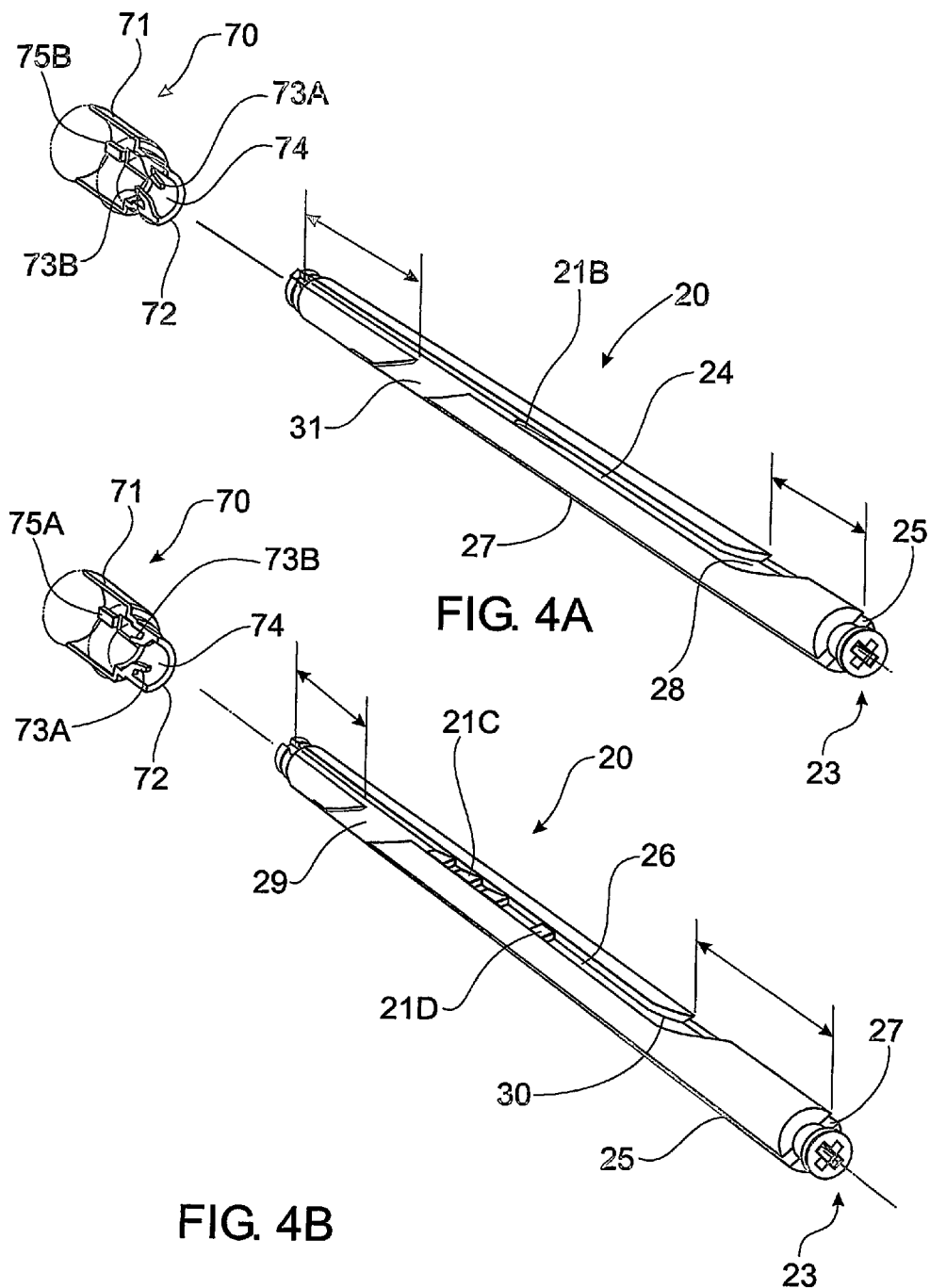
FIGS. 4A and 4B are exploded perspective views of a plunger and a first body member of a spring retainer housing.

An understanding of the operation of plunger 20, with particular regard to rotation of plunger 20 and alignment of needle engaging means 23 with retractable needle barbs 52A, 52B to facilitate needle 50 retraction can be gained by referring now to FIG. 4A and FIG. 4B.

Plunger 20 includes first slot 24, second slot 25, retraction slot 26 and fourth slot 27. First slot 24 is interconnected to second slot 25 via first deviation 28, second slot 25 is interconnected to retraction slot 26 via second deviation 29, retraction slot 26 is interconnected to fourth slot 27 via third deviation 30 and fourth slot 27 is interconnected to first slot 24 via fourth deviation 31. First slot 24 and retraction slot 26 are longitudinally offset with respect to each other; second slot 25 and fourth slot 27 are longitudinally offset with respect to each other; first deviation 28 and third deviation 30 are longitudinally offset with respect to each other; and second deviation 29 and fourth deviation 31 are longitudinally offset with respect to each other; as indicated by arrows in FIG. 4A and FIG. 4B.

Second slot 25 comprises plurality of abutments 21A, first slot 24 includes first slot abutment 21B and retraction slot 26 includes plurality of retraction abutments 21C and lockout abutment 21D.

In FIGS. 4A and 4B, there is also shown first body member 70 of spring retainer 60 which comprises body 71 and collar 72 having first plunger aperture 74 that slidably accommodates plunger 20, and first finger or projection 73A and second finger or projection 73B which are oriented so as to be longitudinally opposed to each other. First body member 70 further comprises respective tabs 75A, 75B inside body 71.

In use, first finger or projection 73A and second finger or projection 73B engage a respective corresponding slot 24, 25, 26, or 27 as in FIG. 4A or as in FIG. 4B.

Fingers 73A, 73B can respectively engage abutments 21A, 21B, 21C in slots of plunger 20 to facilitate prevention of re-use of plunger 20, in a manner similar to that described in International Publication WO 01/80930, as will be described in more detail hereinafter.

In an alternative embodiment, projections 73A, 73B may be spherical or approximately so, to thereby smoothly, slidably engage slots that are appropriately configured to receive such spherical projections.

Figure 5:
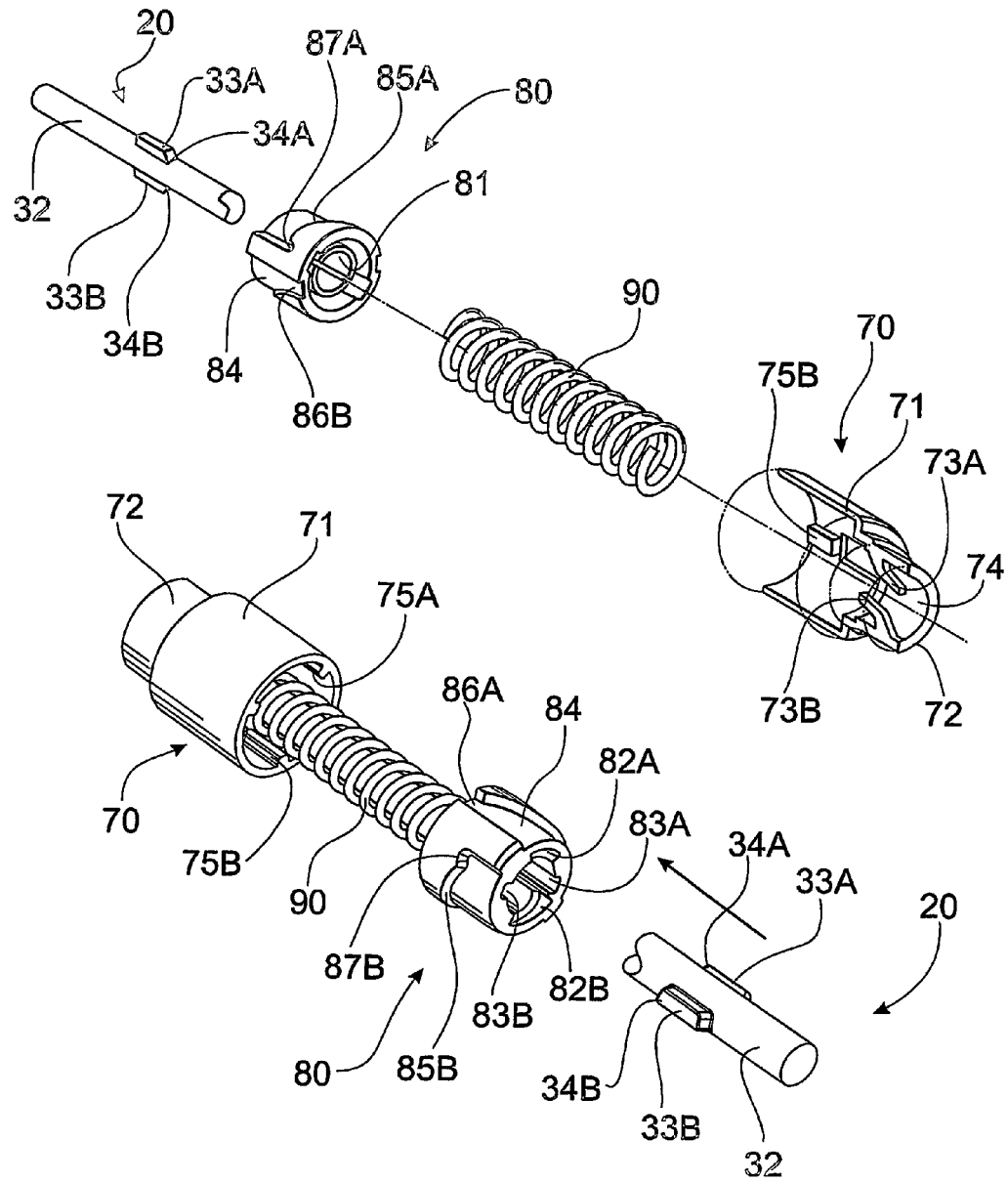
FIG. 5 is an exploded perspective view of spring retainer, spring and plunger.

Referring now to FIG. 5, spring retainer 60 comprises first body member 70 and second body member 80 that when fitted together, co-operate to releasably maintain spring 90 in an initial, compressed state.

Second body member 80 comprises second plunger aperture 81 that slidably accommodates plunger 20. Second body member 80 also comprises shoulder ramps 82A, 82B and shoulder recesses 83A, 83B. Also present on external wall 84 of second body member 80 are circumferential ramps 85A, 85B which at one end have respective guides 86A, 86B and at an opposite end have respective scalloped recesses 87A, 87B.

First body member 70 and second body member 80 are fitted together on plunger 20 to compress spring 90 by way of guides 86A, 86B in sidewall 84 of second body member 80 receiving respective tabs 75A, 75B of first body member 70 and rotating second body member 80 relative to first body member 70 so that tabs 75A, 75B respectively fit into scalloped recesses 87A, 87B.

When spring retainer 60 is assembled, second body member 80 is capable of limited, longitudinal or telescopic movement relative to first body member 70 against the action of compressed spring 90 without disengaging tabs 75A, 75B from scalloped recesses 87A, 87B and hence without inadvertently disengaging second body member 80 from first body member 70.

Typically, this movement is limited to 0.1 to 1.0 mm, preferably to about 0.2 to 0.8 mm or advantageously to about 0.5 mm, although this is readily varied according to the length and/or volume of the syringe, plunger and/or spring.

Engagement between tabs 75A, 75B and scalloped recesses 87A, 87B limits rotation of second body member 80 relative to first body member 70 to no more than about 5°.

Rotation of plunger 20 during syringe filling, injection and needle 50 retraction may best be understood with reference to FIG. 4A and FIG. 4B and also with reference to International Publication WO 01/80930

Initially, in use, first projection 73A is located in first slot 24 and second projection 73B is located in retraction slot 26.

Withdrawal of plunger 20 is followed by first projection 73A slidably moving from first slot 24 into second slot 25 via first deviation 28 and second projection 73B slidably moving from retraction slot 26 into fourth slot 27 via third deviation 30. This causes a 90° rotation of plunger 20 with respect to barrel 50.

During withdrawal of plunger 20, shoulders 33A, 33B are free to slidably travel through respective shoulder recesses 83A, 83B in second body member 80.

Depression of plunger 20 to inject or expel material from barrel 40 occurs when first projection 73A is slidably located in second slot 25 and second projection 73B is slidably located in fourth slot 27.

Accordingly, at this point barb-engaging apertures 22 of plunger 20 are aligned so as to be engageable with barbed arms 52A, 52B of retractable needle 50.

During depression, spring 90 remains compressed by spring retainer 60 and only towards the end of depression of plunger 20 can decompression of spring 90 occur.

Figure 6:
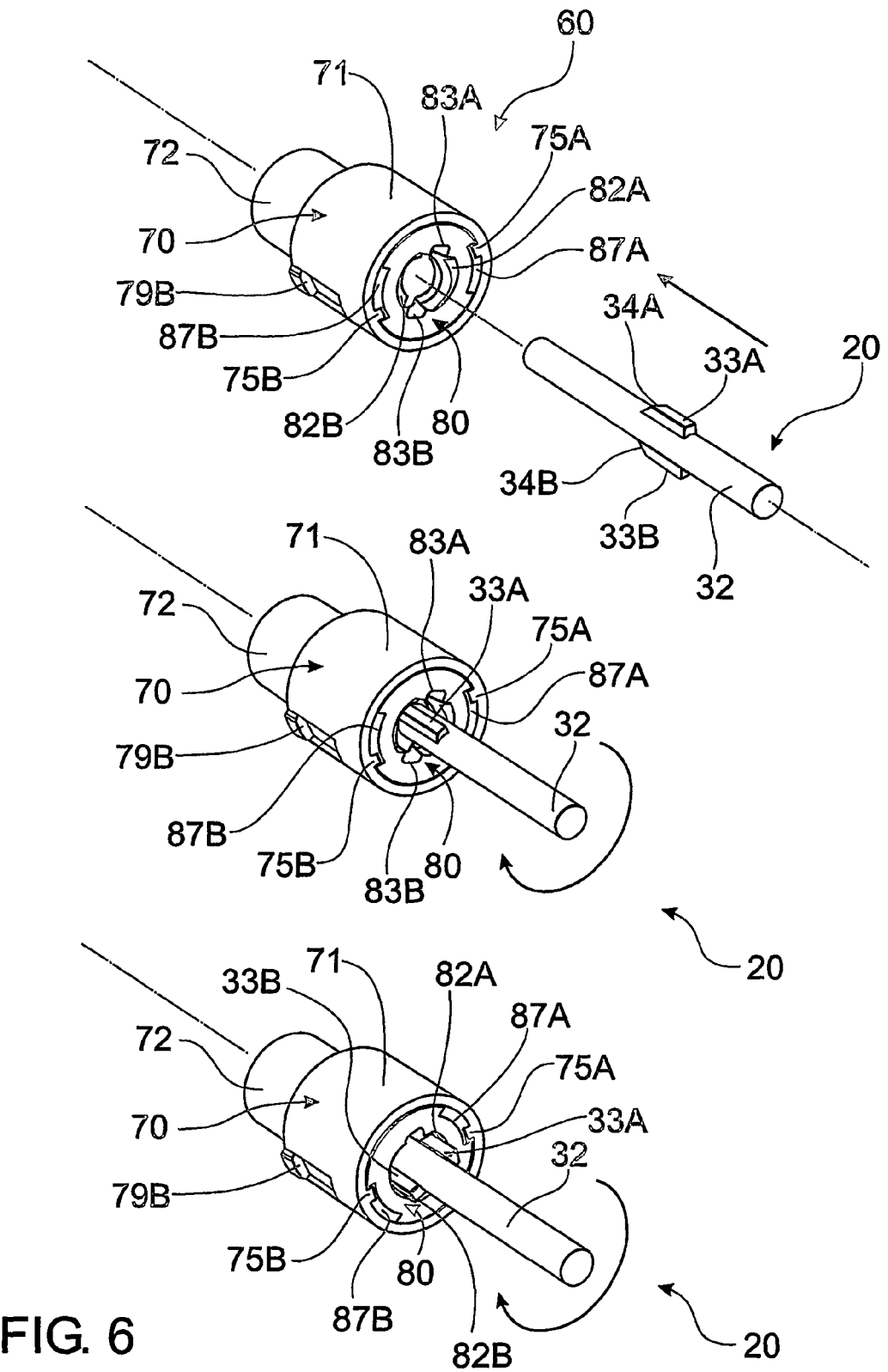
FIG. 6 is an exploded perspective view of spring retainer and plunger.

Initiation of disengagement of second body member 80 from first body member 70 is shown on FIG. 6, where inclined surfaces 34A, 34B of shoulders 33A, 33B of plunger 20 engage respective shoulder ramps 82A, 82B to move second body member 80 longitudinally to further compress spring 90. This is accompanied by barb-engaging apertures 22 respectively engaging barbs 52A, 52B of retractable needle 50 to thereby couple plunger 20 to retractable needle 50.

It is noted that inclined surfaces 34A, 34B of respective shoulders 33A, 33B of plunger 20 ensure only "last-minute" engagement of shoulder ramps 82A, 82B in second body member 80 at the very end of plunger 20 depression.

Longitudinal movement of second body member 80 relative to first body member 70 is driven by lineal movement of plunger 20 which itself is unable to rotate because of first projection 73A engaging second slot 25 and second projection 73B engaging fourth slot 27 of plunger 20. Force applied to plunger 20 by the user during plunger 20 depression is transferred to second body member 80 via engagement between inclined surfaces 34A, 34B of respective shoulders 33A, 33B and shoulder ramps 82A, 82B in second body member 80, which rotates second body member 80 relative to first body member 70 (which cannot rotate) enough to release engagement of scalloped recesses 87A, 87B by respective tabs 75A, 75B. This release initiates disengagement of second body member 80 from first body member 70, thereby allowing spring 90 to decompress which, in turn, forces circumferential ramps 85A, 85B of second body member 80 to slide against tabs 75A, 75B of first body member 70 (which cannot rotate), thereby forcing rotation of second body member 80 relative to first body member 70 as it disengages first body member 70. This force is relayed to plunger 20 by second body member 80 bearing against shoulders 33A, 33B of plunger 20 thereby forcing rotation and retraction of plunger 20 and retractable needle 50.

This is the final 90° plunger rotation wherein first projection 73A moves into retraction slot 26 via second deviation 29 and second projection 73B moving from fourth slot 27 via fourth deviation 31 into first slot 24.

At this point, and in a manner similar to that described in International Publication WO 01/80930, retractable needle 50 and plunger 20 coupled thereto are retracted into a final inoperable position, whereby projections 73B, 73A respectively engage abutment 21B in first slot 24 and abutment 21D in retraction slot 26 to prevent depression or further withdrawal of plunger 20 after retraction of retractable needle 50 into barrel 40.

Figure 7:
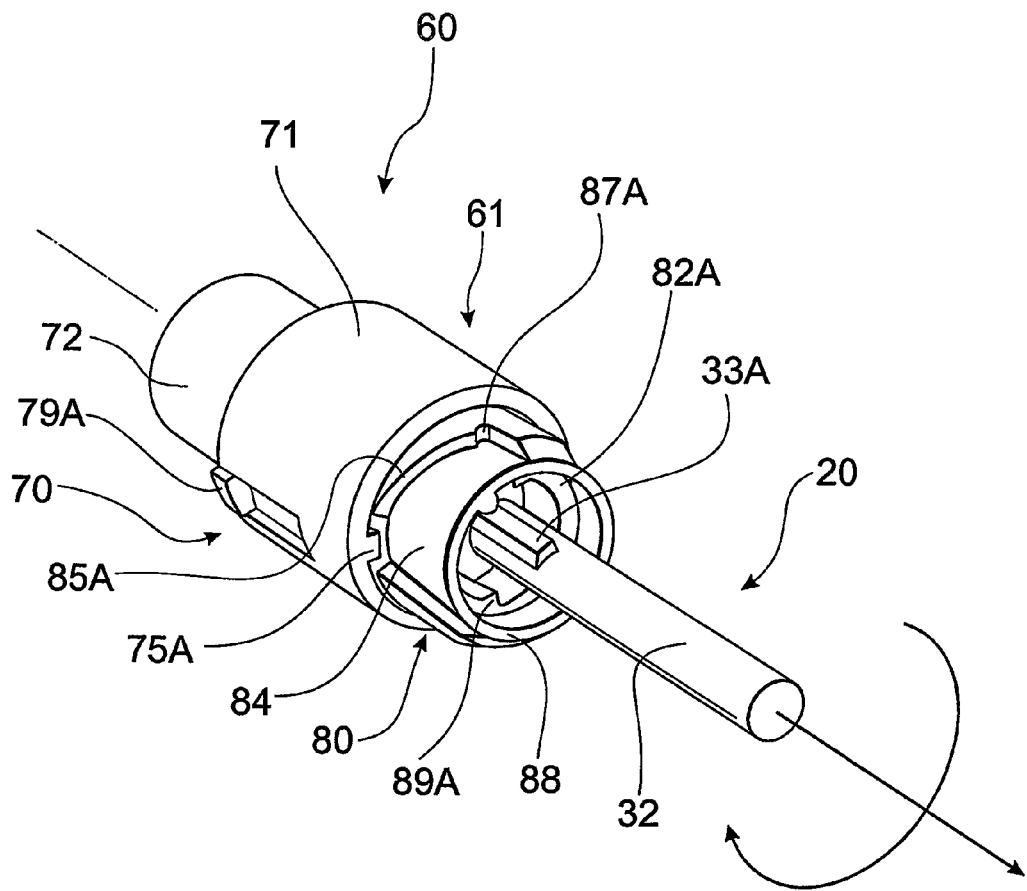
FIG. 7 is an exploded perspective view of disengagement of a first body member and a second body member of a spring retainer.

In an embodiment shown in FIG. 7, as second body member 80 becomes disengaged from first body member 70, it travels axially with plunger 20, driven by decompressed spring 90. Accordingly, second body member 80 travels axially until circumferential ramps 85A, 85B are respectively engaged by tabs 75A, 75B in first body member 70 thereby forcing second body member 80 to rotate in the direction shown by the arrow, which in turn rotates plunger 20 by virtue of engagement between shoulders 33A, 33B of plunger 20 and shoulder ramps 82A, 82B of second body member 80.

By aligning projections 73A, 73B of first body member 70 respectively with second deviation 29 and fourth deviation 31, coupled to the rotation of plunger 20 caused by rotation of second body member 80, rotation of plunger 20 into the aforementioned final, inoperable position is thereby assisted by rotation of second body member 80.

This minimizes the likelihood of a situation where plunger 20 could fail to rotate fully and jam further plunger 20 movement, thereby leaving retractable needle 50 only partially retracted.

It will also be apparent that the embodiment of second body member 80 shown in FIG. 7 has extended neck portion 88 wherein shoulder ramps 82A, 82B are somewhat recessed inside second body member 80 compared to the embodiment shown in FIG. 4 or FIG. 5, for example. This assists prevention of a user tampering with engagement between plunger 20 and second body member 80 by effectively "burying" this inside second body member 80.

Also present are ribs 89A, 89B which engage shoulders 33A, 33B of plunger 20 and prevent a user forcing rotation of plunger 20 relative to second body member 80.

It will also be appreciated that by plunger shoulders 33A, 33B having sufficient length (longitudinally along plunger shaft 21), it is possible to prevent rotation of plunger 20 when projections 73A, 73B have not yet respectively engaged retraction slot 26 and first slot 24 at the start of plunger 20 withdrawal. This assists prevention of a user seeking to rotate plunger 20 back into an operable position before withdrawal has commenced.

It will therefore be apparent from the foregoing that it is only at the very end of plunger 20 depression that decompressed spring 90 acts in facilitating plunger 20 and retractable needle 50 withdrawal. This provides a much smoother feel to the operation of the syringe without any significant spring 90 resistance being felt during most stages of injection.

Another advantage provided by the spring retainer 60 of the invention is that it can accommodate a spring 90 of various sizes, such as being operable with varying needle sizes and syringe sizes. In the higher volume syringes with longer needles, the length of spring 90 required to facilitate retraction of plunger 20 may be too great to fit easily on plunger 20 external to barrel 40. Spring retainer 60 compresses spring 90 into a manageable size despite the uncompressed length of spring 90.

Throughout the specification, the aim has been to describe the preferred embodiments of the invention without limiting the invention to any one embodiment or specific collection of features. Various changes and modifications may be made to the embodiments described and illustrated without departing from the present invention.

For example, plunger means for engaging second body member 80 and the respective, complementary mating portions on second body member 80 may be any suitable arrangement not limited to shoulders 33A, 33B and shoulder ramps 82A, 82B as described herein.

Further to this, although tabs 75A, 75B and scalloped recesses 87A, 87B are examples of means for releasably coupling said first body member 70 and second body member 80, the invention contemplates any other arrangements that utilize complementary mating portions on first body member 70 and second body member 80 to facilitate releasable coupling of said first body member 70 and second body member 80 to form said housing and thereby maintain spring 90 in an initial compressed state.

It should also be appreciated that the invention contemplates an alternative embodiment wherein circumferential ramps 85A, 85B are replaced by respective channels or guide slots which allow tabs 75A, 75B to move longitudinally during disengagement of first body member 70 and second body member 80, without forcing rotation of second body member 80 and plunger 20 engaged therewith.

It is also contemplated that abutments 21A, 21B, 21C and 21D described herein may be in the form of ledges, gates, ridges or any other means for restricting plunger movement as desired by the skilled person.

The invention claimed is:

1. A spring retainer for a syringe that comprises a barrel, a plunger, a spring and a retractable needle, said spring retainer comprising a housing having first and second body members adapted to releasably maintain said spring in a compressed state until rotational disengagement of said first and second body members allows decompression of said spring to facilitate retraction of said retractable needle into said barrel, wherein the second body member is adapted to be engageable by said plunger so that depression of said plunger triggers said rotational disengagement of said second body member relative to said first body member, wherein said second body member further comprises circumferential ramps arranged so that decompression of said spring forces engagement of said ramps by tabs to facilitate rotation of said second body member relative to said first body member.

2. The spring retainer of claim 1, wherein the first body member comprises two or more projections capable of slidably engaging respective slots in said plunger to guide rotation of said plunger in use.

3. The spring retainer of claim 2, wherein said second body member comprises one or more recesses arranged so as to be releasably engageable by respective tabs on said first body member.

4. A syringe comprising a barrel, a plunger, a spring, a spring retainer, and a retractable needle which is capable of coupling with said plunger for retraction of said needle into said barrel, said spring retainer comprising a housing having a first body member that comprises two or more projections capable of slidably engaging respective slots in said plunger to guide rotation of said plunger in use and a second body member, said first and second body members adapted to releasably maintain said spring in a compressed state until disengagement of said first and second body members allows decompression of said spring to facilitate retraction of said retractable needle into said barrel, wherein the second body member is adapted to be engageable by said plunger so that depression of said plunger triggers rotational disengagement of said first body member and said second body member.

5. The syringe of claim 4, wherein said second body member comprises one or more recesses arranged so as to be engageable by respective tabs on said first body member.

6. The syringe of claim 5, comprising one or more plunger elements that engage respective complementary mating portions on said second body member.

7. The syringe of claim 6, wherein the one or more plunger elements comprise two shoulders engageable with respective shoulder ramps on said second body member.

8. The syringe of claim 7, arranged so that upon engagement between said two shoulders and respective shoulder ramps on said second body member, rotation of said shoulders selectively rotates said second body member relative to said first body member thereby disengaging said tabs from said recesses which disengages said first body member and said second body member to allow decompression of said spring.

9. The syringe of claim 8, wherein said second body member further comprises circumferential ramps arranged so that decompression of said spring forces engagement of said ramps by said tabs to facilitate rotation of said second body member relative to said first body member.

10. The syringe of claim 9, arranged so that rotation of said second body member is capable of assisting rotation of said plunger into a final, inoperable position.

11. The syringe of claim 4, having said retractable needle mounted thereto, whereby in use said spring is maintained in a compressed state by said spring retainer until at or near completion of depression of said plunger when injecting material from said syringe.

12. The syringe of claim 11, arranged so that said plunger and said retractable needle are coupled at or near completion of depression of said plunger.

13. The syringe of claim 4, arranged so that disengagement of said first and second body members of said housing can facilitate rotation of said second body member relative to said first body member.

14. The syringe of claim 13, arranged so that rotation of said second body member is capable of assisting rotation of said plunger, when said retractable needle is coupled therewith, into a final, inoperable position.

15. The syringe of claim 14, wherein said first body member comprises two or more projections capable of bearing against respective abutments in respective slots in said plunger to maintain said plunger in said final, inoperable position.

16. A spring retainer for a syringe that comprises a barrel, a plunger, a spring and a retractable needle, the spring retainer comprising a housing having first and second body members adapted to releasably maintain the spring in a compressed state until rotational disengagement of the first and second body members allows decompression of the spring to facilitate refraction of the retractable needle into the barrel, wherein the second body member is adapted to be engageable by said plunger so that depression of said plunger triggers said rotational disengagement of said first body member and said second body member and wherein the first body member comprises two or more projections capable of slidably engaging respective slots in the plunger to guide rotation of the plunger in use.

* * * * *